United States Patent [19]

Glamkowski et al.

[11] Patent Number: 4,952,588
[45] Date of Patent: Aug. 28, 1990

[54] 1-ARYL-3-QUINOLINE-AND 1-ARYL-3-ISOQUINOLINE-CARBOXAMIDES

[75] Inventors: Edward J. Glamkowski, Warren; R. Richard L. Hamer, Westfield, both of N.J.

[73] Assignee: Hoechst-Roussel Pharmaceuticals Inc., Somerville, N.J.

[21] Appl. No.: 401,386

[22] Filed: Aug. 31, 1989

Related U.S. Application Data

[62] Division of Ser. No. 218,783, Jul. 14, 1988, abandoned, which is a division of Ser. No. 125,971, Nov. 27, 1987, Pat. No. 4,786,644.

[51] Int. Cl.$^5$ .................. A61K 31/435; C07D 217/22
[52] U.S. Cl. ........................ 514/309; 546/141; 546/142
[58] Field of Search ................. 514/309; 546/141, 142

[56] References Cited

U.S. PATENT DOCUMENTS 4,772,613  9/1988  Parsons et al. ..................... 546/141

Primary Examiner—John M. Ford
Assistant Examiner—J. Richter
Attorney, Agent, or Firm—Raymond R. Wittekind

[57] ABSTRACT

Novel 1-aryl-3-quinolinecarboxamides and 1-aryl-3-isoquinolinecarboxamides, processes for the preparation thereof, and methods for treating pain and inflammation utilizing compounds and compositions thereof are disclosed.

13 Claims, No Drawings

1-ARYL-3-QUINOLINE-AND 1-ARYL-3-ISOQUINOLINE-CARBOXAMIDES

This is a division, of application Ser. No. 218,783 filed Jul. 14, 1988, now abandoned, which is a divisional of application Ser. No. 125,971 filed Nov. 27, 1987, now U.S. Pat. No. 4,786,644.

This invention relates to 1-aryl-3-quinolinecarboxamides and 1-aryl-3-isoquinolinecarboxamides of the formula:

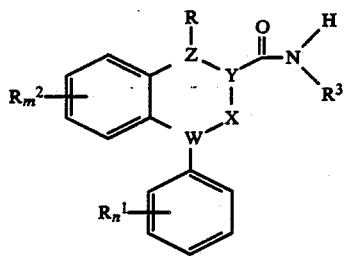

FORMULA I wherein WXYZR is a bivalent radical selected from the group consisting of N—CH=C—C=O, N—CH$_2$—CH—C=O, N—CH$_2$—C=C—OH, C=N—CH—C=O, and C=N—C=C—OH; $R^1$ and $R^2$ are monovalent radicals independently selected from the group consisting of halogen, loweralkyl and loweralkoxy; $R^3$ is a substituted or unsubstituted monovalent radical selected from the group consisting of phenyl, pyridyl, pyrimidyl, pyrazinyl, triazinyl, thiazolyl, thiadiazolyl, isoxazolyl, oxadiazolyl, quinolyl, isoquinolyl, and benzothiazolyl; and m and n are integers independently having values of zero or 1; the optical antipodes and pharmaceutically acceptable acid addition salts thereof. The 1-aryl-3-quinolinecarboxamides and 1-aryl-3-isoquinolinecarboxamides of the present invention are useful as antiinflammatory and analgetic agents.

In a preferred embodiment this invention relates to Formula I compounds wherein $R^3$ is selected from the group consisting of substituted and unsubstituted phenyl, pyridyl, pyrazinyl, thiazolyl, isoxazolyl, and benzothiazolyl radicals.

Subgeneric to the quinoline and isoquinolinecarboxamides of this invention are Formula I compounds wherein:

(a) $R^3$ is a phenyl radical of the formula:

wherein $R^4$ is a radical selected from the group consisting of loweralkyl, loweralkoxy, trifluoromethyl, nitro, or halogen and p is an integer having a value from zero to 5, inclusive, wherein for each value of p, $R^4$ may be the same or different;

(b) $R^3$ is a pyridyl radical of the formula:

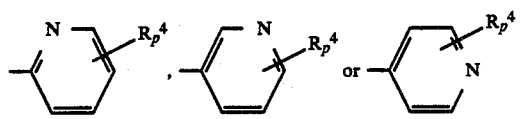

wherein $R^4$ is a radical selected from the group consisting of loweralkyl, loweralkoxy, or halogen and p is an integer having a value from zero to 4, inclusive, wherein for each value of p, $R^4$ may be the same or different;

(c) $R^3$ is a pyrimidyl radical of the formula:

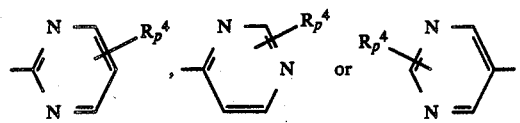

wherein $R^4$ is a radical selected from the group consisting of loweralkyl, loweralkoxy, or halogen and p is an integer having a value from zero to 2, inclusive, wherein for each value of p, $R^4$ may be the same or different;

(d) $R^3$ is a pyrazinyl radical of the formula:

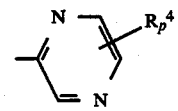

wherein $R^4$ is a radical selected from the group consisting of loweralkyl, loweralkoxy, or halogen and p is an integer having a value from zero to 2, inclusive, wherein for each value of p, $R^4$ may be the same or different;

(e) $R^3$ is a thiazolyl radical of the formula:

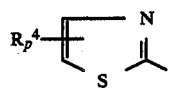

wherein $R^4$ is a radical selected from the group consisting of loweralkyl, loweralkoxy, or halogen and p is an integer having a value of zero or 1;

(f) $R^3$ is a triazinyl radical of the formula:

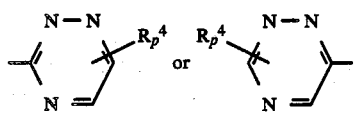

wherein $R^4$ is a radical selected from the group consisting of loweralkyl, loweralkoxy, or halogen and p is an integer having a value from zero to 2, inclusive, wherein for each p, $R^4$ may be the same or different;

(g) $R^3$ is a thiadiazolyl radical of the formula:

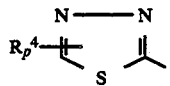

wherein $R^4$ is a radical selected from the group consisting of loweralkyl, loweralkoxy, or halogen and p is an integer having a value of zero or 1;

(h) $R^3$ is an isoxazolyl radical of the formula:

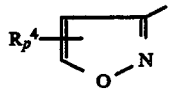

wherein $R^4$ is a radical selected from the group consisting of loweralkyl, loweralkoxy, or halogen and p is an integer having a value of zero or 1;

(i) $R^3$ is an oxadiazolyl radical of the formula:

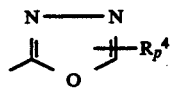

wherein $R^4$ is a radical selected from the group consisting of loweralkyl, loweralkoxy, or halogen and p is an integer having a value of zero or 1;

(j) $R^3$ is a 2-, 3-, 4-, 5-, 6-, 7-, or 8-quinolyl radical optionally substituted at either or both ring(s) thereof by up to two substituents independently selected from the group consisting of loweralkyl, loweralkoxy, or halogen, said substituent(s) being attached to said ring(s) at other than a nitrogen atom;

(k) $R^3$ is an isoquinolyl radical of the formula:

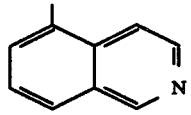

optionally substituted at either or both ring(s) thereof by up to two substituents independently selected from the group consisting of loweralkyl, loweralkoxy, or halogen said substituents(s) being attached to said ring(s) at other than a nitrogen atom;

(l) $R^3$ is a benzothiazolyl radical of the formula:

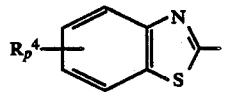

wherein $R^4$ is a radical selected from the group consisting of loweralkyl, loweralkoxy, or halogen and p is an integer having a value from zero to 4, inclusive, wherein for each value of p, $R^4$ may be the same or different;

(m) m is zero; and (o) n is zero.

As used throughout the specification and appended claims, the following definitions shall apply:

"Loweralkyl"-a linear or branched acyclic hydrocarbon radical containing no unsaturation and having the formula $-C_xH_{2x+1}$ wherein x is an integer having a value of 1 to 7, inclusive, such as methyl, ethyl, 1-propyl, 2-propyl, 1-butyl, 1-pentyl, 2-pentyl, 3-hexyl, 4-heptyl, and the like. Preferred loweralkyls are those radicals wherein x has a value of 1 or 2.

"Loweralkoxy"-an acyclic organic radical of the formula $-OC_xH_{2x+1}$ wherein x is an integer having a value of 1 to 7, inclusive, such as methoxy, ethoxy, 1- and 2-propoxy, 1,2-dimethylethoxy, 1-butoxy, 1-and 2-pentoxy, 3-hexoxy, 4-heptoxy and the like. Preferred loweralkoxys are those radicals wherein x has a value of 1 or 2.

"Halogen"-a member of the group consisting of fluorine, chlorine, bromine, and iodine radicals. Preferred halogens are bromine or chlorine radicals.

"Aryl"-a phenyl group optionally substituted by up to 5 substituents each of which is independently loweralkyl, loweralkoxy, halogen, or trifluoromethyl.

The 1-aryl-3-quinolinecarboxamides and 1-aryl-3-isoquinolinecarboxamides of this invention are synthesized by the processes illustrated in the Reaction Schemes which follow. As illustrated in Reaction Scheme A, the subject quinolinecarboxamides are produced by converting a 1-aryl-2,3-dihydro-4-(1H)-quinoline 1 to an ethyl ester of 1-aryl-1,2-dihydro-4-hydroxy-3-quinolinecarboxylic acid 2 which is treated with an arylamine 3 to produce a 1-aryl-4-hydroxy-3-quinolinecarboxamide 4 (existing as tautomers 4a and 4b) which is optionally oxidized to the corresponding 4-oxo derivative 5.

The preparation of 2,3-dihydro-1-phenyl-4-(1H)-quinolones 1 is well known in the art. See for example, Hurd, C. D. et al. J. Am. Chem. Soc., 76, 5065 (1954) describing the production of 2,3-dihydro-4-(1H)-quinolones by the cyclization of N,N-diphenyl-β-alanine utilizing polyphosphoric acid as a ring closing reagent. Conversion of the quinolone 1 is accomplished by treatment with diethylcarbonate in the presence of an alkali metal hydride (e.g. potassium hydride, sodium hydride, lithium hydride, and the like, sodium hydride being preferred). Typically, the condensation is conducted in the presence of a suitable organic solvent at a temperature of from about 20° to the reflux temperature of the solvent medium. Preferably the reaction is conducted under reflux conditions. Suitable solvents include aromatic hydrocarbons, such as, for example, benzene, xylene, toluene and the like, dimethylsulfoxide, or dimethylformamide. Benzene is preferred.

Aminolysis of the ester 2 by treatment with an aryl amine 3 is ordinarily conducted in the presence of an appropriate organic solvent at a temperature of from about 20° to the reflux temperature of the solvent medium. Preferably the reaction is conducted under reflux conditions. Suitable solvents include ethereal solvents such as tetrahydrofuran, diethyl ether, 1,2-dimethoxyethane, dioxane, and the like. Tetrahydrofuran is preferred.

Oxidation of the carboxamide 4 is achieved by treatment with an appropriate oxidizing agent (e.g. manganese dioxide, barium permanganate, and the like) at a temperature of from about 0° to the reflux temperature of the solvent medium. Desirably the oxidation is conducted in the presence of a suitable organic solvent (e.g. hydrocarbons or halocarbons such as, for example, benzene, toluene, xylene, dichloroethane, chloroform, and the like).

As illustrated in Reaction Scheme B, 1-aryl-3-isoquinolinecarboxamides 7 (existing as tautomers 7a and 7b) are produced by aminolysis of a 1-aryl-4-hydroxy-3-isoquinolinecarboxylic acid, ethyl ester 6. The preparation of ethyl esters of 1-aryl-4-hydroxy-3-isoquinolinecarboxylic acid is well known in the art. See, for example, Marsili et al., Ann. Chim. 52, 112 (1962). Aminolysis of the ester 6 is accomplished by treatment with an aryl amine 3 in the presence of a non-reactive organic solvent at a temperature of from about 20° to the reflux temperature of the solvent medium. Suitable solvents include ethereal solvents and hydrocarbons such as, for example, tetrahydrofuran, diethyl ether, 1,2-dimethoxyethane, dioxane, benzene, toluene, xylene, and the like. Solvent preference is subject to variation depending upon the particular aryl amine 3 reacted. In general, benzene or tetrahydrofuran are preferred. Desirably, the reaction is conducted under basic conditions. Suitable bases include alkali metal hydrides, sodium hydride being preferred. In order to increase product yield, it is recommended that the reaction be conducted in an ultrasonic bath.

Included among the compounds of this invention are the following:

4-hydroxy-N-(4-methoxyphenyl)-1-phenyl-3-isoquinolinecarboxamide;
1,4-dihydro-4-oxo-1-phenyl-N-[2-(trifluoromethyl)-phenyl]-3-quinolinecarboxamide;
1,2-dihydro-4-hydroxy-N-(3-nitrophenyl)-1-phenyl-3-quinolinecarboxamide;
3,4-dihydro-N-(2-fluorophenyl)-4-oxo-1-phenyl-3-isoquinolinecarboxamide;
4-hydroxy-N-(5-nitro-2-pyridyl)-1-phenyl-3-isoquinolinecarboxamide;
3,4-dihydro-N-(5-bromo-2-pyridyl)-4-oxo-1-phenyl-3-isoquinolinecarboxamide;
4-hydroxy-N-(3-nitro-2-pyridyl)-1-phenyl-3-isoquinolinecarboxamide;
4-hydroxy-N-(3-chloro-2,5,6-trifluoro-4-pyridyl)-1-phenyl-3-isoquinolinecarboxamide;
1,2-dihydro-4-hydroxy-N-(2-methoxy-5-pyridyl)-1-phenyl-3-quinolinecarboxamide;
1,4-dihydro-N-(4,6-dimethyl-2-pyridyl)-4-oxo-1-phenyl-3-quinolinecarboxamide;
1,2-dihydro-4-hydroxy-1-phenyl-N-(2,3,5,6-tetrafluoro-4-pyridyl)-3-quinolinecarboxamide;
1,2-dihydro-N-(3,5-dibromo-2-pyridyl)-4-hydroxy-1-phenyl-3-quinolinecarboxamide;
1,4-dihydro-N-(4-methyl-2-pyridyl)-4-oxo-1-phenyl-3-quinolinecarboxamide;
1,2-dihydro-4-hydroxy-1-phenyl-N-(4-pyrimidyl)-3-quinolinecarboxamide;
1,4-dihydro-4-oxo-1-phenyl-N-(2-pyrimidyl)-3-quinolinecarboxamide;
4-hydroxy-N-(4-methyl-2-pyrimidyl)-1-phenyl-3-isoquinolinecarboxamide;
1,2-dihydro-4-hydroxy-N-(4-chloro-6-methyl-2-pyrimidyl)-1-phenyl-3-quinolinecarboxamide;
4-hydroxy-1-phenyl-N-(2-pyrazinyl)-3-isoquinolinecarboxamide;
1,2-dihydro-4-hydroxy-1-phenyl-N-(1,2,4-triazin-3-yl)-3-quinolinecarboxamide;
1,2-dihydro-N-(5,6-dimethyl-1,2,4-triazin-3-yl)-4-hydroxy-1-phenyl-3-quinolinecarboxamide;
4-hydroxy-N-(2-chloro-5-thiazolyl)-1-phenyl-3-isoquinolinecarboxamide;
1,2-dihydro-N-(4,5-dimethyl-2-thiazolyl)-4-hydroxy-1-phenyl-3-quinolinecarboxamide;
4-hydroxy-1-phenyl-N-(1,3,4-thiadiazol-2-yl)-3-isoquinolinecarboxamide;
1,4-dihydro-N-(5-ethyl-1,3,4-thiadiazol-2-yl)-4-oxo-1-phenyl-3-quinolinecarboxamide;
1,2-dihydro-4-hydroxy-1-phenyl-N-(2-mercapto-1,3,4-thiadiazol-5-yl)-3-quinolinecarboxamide;
4-hydroxy-N-(5-nitro-2-thiazolyl)-1-phenyl-3-isoquinolinecarboxamide;
4-hydroxy-N-(5-methyl-1,3,4-oxadiazol-2-yl)-1-phenyl-3-isoquinolinecarboxamide;
4-hydroxy-1-phenyl-N-(3-quinolyl)-3-isoquinolinecarboxamide;
3,4-dihydro-4-oxo-1-phenyl-N-(5-quinolyl)-3-isoquinolinecarboxamide;
1,2-dihydro-4-hydroxy-1-phenyl-N-(6-quinolyl)-3-quinolinecarboxamide;
1,4-dihydro-4-oxo-1-phenyl-N-(8-quinolyl)-3-quinolinecarboxamide;
1,2-dihydro-4-hydroxy-N-(2-methyl-4-quinolyl)-1-phenyl-3-quinolinecarboxamide;
1,2-dihydro-4-hydroxy-N-(5-isoquinolyl)-1-phenyl-3-quinolinecarboxamide;
1,2-dihydro-4-hydroxy-N-(4-methoxy-2-benzothiazolyl)-1-phenyl-3-quinolinecarboxamide;
1,2-dihydro-N-(5,6-dimethyl-2-benzothiazolyl)-4-hydroxy-1-phenyl-3-quinolinecarboxamide;
1,2-dihydro-6,7-dimethyl-4-hydroxy-1-phenyl-N-phenyl-3-quinolinecarboxamide;
6-chloro-1,2-dihydro-4-hydroxy-1-phenyl-N-phenyl-3-quinolinecarboxamide;
6,7-dichloro-1,4-dihydro-4-oxo-1-phenyl-N-(2-pyridyl)-3-quinolinecarboxamide;
1,2-dihydro-6,7-dimethoxy-4-hydroxy-1-phenyl-N-(4-methyl-2-thiazolyl)-3-quinolinecarboxamide;
1,2-dihydro-1-(4-chlorophenyl)-4-hydroxy-1-N-phenyl-3-quinolinecarboxamide;
1,2-dihydro-4-hydroxy-1-(4-methylphenyl)-N-(2-pyrazinyl)-3-quinolinecarboxamide; and
4-oxo-1-phenyl-1,2,3,4-tetrahydro-N-(2-thiazolyl)-3-quinolinecarboxamide.

The compounds of the present invention are useful as antiinflammatory agents due to their ability to suppress inflammation in mammals. The activity of the compounds is demonstrated in the carrageenan-induced rat paw edema antiinflammatory assay [Proc. Soc. Exptl. Biol. Med., 111, 544 (1962), and J. Pharmacol. Exp., 166, 90 (1969)]. The results of the antiiflammatory test of some of the compounds of this invention are given in Table 1.

TABLE 1

| Inhibition of Carrageenan-Induced Rat Paw Edema | |
|---|---|
| Compound | Percent Inhibition[1] |
| 1,2-dihydro-4-hydroxy-1-phenyl-N-phenyl-3-quinolinecarboxamide | −28% |
| 1,2-dihydro-4-hydroxy-1-phenyl-N-2-pyrazinyl-3-quinolinecarboxamide | −24% |
| 1,4-dihydro-4-oxo-1-phenyl-N-(2-pyridinyl)-3-quinolinecarboxamide | −25% |
| 1,4-dihydro-4-oxo-1-phenyl-N-(2-pyrazinyl)-3-quinolinecarboxamide | −23% |
| 1,4-dihydro-N-(4-methyl-2-thiazolyl)-4-oxo-1-phenyl-3-quinolinecarboxamide | −28% |
| Aspirin | −29% |

[1] at a screening dose of 100 mg/kg, p.o.

The antiiflammatory activities of the compounds of this invention are also demonstrated in the adjuvant-induced polyarthritis syndrome in rats. This activity was measured by a procedure similar to that described by C. M. Pearson and F. D. Wood, Arthritis and Rheumatism, 2, 440 (1959).

Groups of 10 male Charles River-Wistar Lewis rats weighing 150 to 175 g were individually housed and maintained on a regular rat chow diet. Water was given ad libitum. The adjuvant was prepared by suspending 75 mg of *Mycobacterium butyricum* (Difco Laboratories, Detroit, Mich.) in 10 ml of white paraffin oil with continuous stirring for 2 hours at room temperature prior to administration. Test compounds are prepared by suspending the drug in water, adding one drop of Tween 80 per 10 ml of suspension, and homogenizing. The adjuvant suspension (0.1 ml) was injected into the footpad of the left hind paw of the rat. Test compound suspensions were administered orally (10 ml/kg) the day before adjuvant suspension injection and the administration was continued daily for 21 days. One group of ten rats was used for the test drug. Standard, adjuvant-injected control and non-injected control groups were run along with the test drug. Control animals received vehicle (10 ml/kg). Injected and non-injected paw volumes were determined on the day the adjuvant suspension was given, and on subsequent days thereafter (usually days 5, 10, 18, and 21) by the method of C. A. Winter et al., Proc. Soc. Exp. Biol. Med., 111, 544 (1962).

The percent inhibition of paw volume (injected and non-injected paw) were calculated by the following formula:

$$\% \text{ Inhibition} = \frac{\substack{\text{Mean Paw Volume}\\\text{Change of Injected}\\\text{(or Non-Injected)}\\\text{Control}} - \substack{\text{Mean Paw}\\\text{Volume Change of}\\\text{Drug Treated}}}{\text{Mean Paw Volume Change of Injected (or Non-Injected) Control}} \times 100$$

The results of the adjuvant-induced polyarthritis syndrome test procedure for several of the compounds of this invention are provided in Table 2.

TABLE 2

| Compound | Adjuvant-Treated Paw | Non-Injected Paw |
|---|---|---|
| 1,2-dihydro-4-hydroxy-1-phenyl-N-phenyl-3-quinolinecarboxamide[2] | −5% | −26% |
| N-(5-bromo-2-pyridinyl)-1,2-dihydro-4-hydroxy-1-phenyl-3-quinoline-carboxamide[2] | −2 | −22% |
| 1,4-dihydro-4-oxo-1-phenyl-N-(2-pyrazinyl)-3-quinolinecarboxamide[2] | −7% | −23% |
| 1,4-dihydro-N-(4-methyl-2-thiazolyl)-4-oxo-1-phenyl-3-quinolinecarboxamide[2] | −12% | −26% |
| 4-hydroxy-1-phenyl-N-(2-pyridyl)-3-isoquinolinecarboxamide[3] | +1% | −17% |
| N-(5-chloro-2-pyridinyl)-4-hydroxy-1-phenyl-3-isoquinolinecarboxamide[2] | −22% | −38% |
| Aspirin[2] | −22% | −33% |

[2]at a screening dose of 50 mg/kg, p.o.
[3]at a screening dose of 45 mg/kg, p.o.

Inflammation inhibition is achieved when the compounds of this invention are administered to a subject requiring such treatment at an effective oral, parenteral, or intravenous dose of from about 1 to about 300 mg/kg of body weight per day. Compounds which achieve effective inflammation inhibition at doses of from about 1 to about 100 mg/kg of body weight per day are particularly desirable. It is to be understood, however, that for any particular subject, specific dosage regimens should be adjusted according to the individual need and professional judgment of the person administering or supervising the administration of same. Doses set forth herein are exemplary only and are not intended to limit the scope or practice of the invention.

The compounds of this invention are also useful as analgesic agents due to their ability to alleviate pain in mammals. The procedure employed to determine analgetic utility is a modification of the phenyl-p-quinone writhing assay in mice, a standard assay for analgetic activity [Proc. Soc. Exptl. Med., 95 729 (1957)]. Pursuant to the modified procedure phenyl-p-benzoquinone (Eastman, 12.5 mg) is dissolved in 5 ml of 95% ethanol and the solution is diluted to a total volume of 100 ml with distilled water. The solution is administered to the subject mice intraperitoneally at a dose of 10 ml per kg of body weight. A characteristic "writhe", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously (s.c.) or orally (p.o.) at 15, 30, 45 and 60 minutes prior to administration of the phenyl-p-quinone. A control group (2 animals per group) receive an equal volume of the vehicle. After the administration of the phenyl-p-quinone, the mice are placed separately in one liter beakers, and after five minutes, are observed for ten minutes. The number of writhes for each animal is recorded. The following formula is used to compute the percent inhibition:

$$\frac{x \text{ Writhes in Control Group} - x \text{ Writhes in Drug Group}}{x \text{ Writhes in Control Group}} \times 100$$

A dose range determination is run in the same manner as the time response except 10 animals per group are tested at the peak time of test drug activity. Fifty animals, 4 test drug groups, and a vehicle control are employed. Animals are dosed and tested in a randomized manner. The time period with the greatest percent of inhibition is considered the peak time.

A calculated $ED_{50}$, i.e., the dose at which the test compound effects a 50% inhibition of writhing, is determined by computer linear regression analysis. The results of the phenyl-p-quinone writhing assay for several of the compounds of this invention are provided in Table 3.

TABLE 3

| Compound | Analgesic Activity % Inhibition of Writhing at a Screening Dose of 20 mg/kg, s.c. |
|---|---|
| N-(3-chlorophenyl)-4-hydroxy-1-phenyl-3-isoquinolinecarboxamide | 51% |
| N-(5-chloro-2-pyridinyl)-4-hydroxy-1-phenyl-3-isoquinolinecarboxamide | 57% |
| 1,2-dihydro-4-hydroxy-1-phenyl-N-(2-pyrazinyl)-3-quinolinecarboxamide | 31% |
| N-(5-bromo-2-pyridinyl)-1,2-dihydro-4-hydroxy-1-phenyl-3-quinolinecarboxamide | 39% |
| 1,2-dihydro-4-hydroxy-N-(4-methyl-2-thiazoyl)-1-phenyl-3-quinolinecarboxamide | 36% |
| 1,4-dihydro-N-(6-methyl-2-pyridinyl)-4-oxo-1-phenyl-3-quinolinecarboxamide | 35% |
| 1,4-dihydro-N-(5-methyl-2-pyridinyl)-4-oxo-1-phenyl-3-quinolinecarboxamide | 30% |
| Aspirin | $ED_{50} = 32.8$ mg/kg s.c. |

Analgesia production is achieved when the compounds of this invention are administered to a subject requiring such treatment at an effective oral, parenteral or intravenous dose of from 1 to 300 mg/kg of body weight per day. Compounds which achieve effective analgesia production at doses of from about 1 to about 100 mg/kg of body weight per day are particularly desirable. It is to be understood, however, that for any particular subject, specific dosage regimens should be adjusted according to the individual need and the professional judgment of the person administering or supervising the administration of the aforesaid compound. It is further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. 1-Aryl-3-quinolinecarboxamides and 1-aryl-3-isoquinolinecarboxamides of this invention, while effective themselves, may be formulated and administered in the form of their pharmaceutically acceptable acid addition salts for purposes of stability, convenience, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, succinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used as the form of tablets, troches, capsules, elixirs, suspensions, syrups, wafers, chewing gums and the like. These preparations should contain at least 0.5% of active compound, but may be varied depending upon the particular form and may conveniently be between 1 to about 70% of the weight of the unit. The amount of active compound in such compositions is such that a suitable dosage will be obtained. Preferred compositions preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Promogel TM, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit form is a capsule, it may contain, in addition to materials of the proceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or other sweetening agents, preservatives, dyes, coloring agents and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

EXAMPLES

The following Examples are for illustrative purposes only and are not to be construed as limiting the invention.

EXAMPLE 1

4-Hydroxy-1-phenyl-N-(2-pyridyl)-3-isoquinolinecarboxamide

To a stirred slurry of 1.14 g of sodium hydride (as a 50% oil dispersion) in 100 ml of benzene was added 2.25 g of 2-aminopyridine. After stirring at room temperature for 15 minutes the slurry was treated with a solution of 2.25 g of 4-hydroxy-1-phenyl-3-isoquinolinecarboxylic acid, ethyl ester in 50 ml of benzene. After refluxing for one hour, the reaction mixture was cooled to room temperature, quenched with water, and extracted with three 100 ml aliquots of hot tetrahydrofuran. The organic layer was dried over magnesium sulfate, filtered, and evaporated to yield 1.7 g (65%) of 4-hydroxy-1-phenyl-N-(2-pyridyl)-3-isoquinolinecarboxamide. Recrystallization from dichloromethane afforded the analytical sample, m.p. 228°–230° C.

ANALYSIS: Calculated for $C_{21}H_{15}N_3O_2$: 73.88% C; 4.42% H; 12.31% N; Found: 73.53% C; 4.48% H; 12.35% N.

EXAMPLE 2

4-Hydroxy-N-(6-methyl-2-pyridyl)-1-phenyl-3-isoquinolinecarboxamide

A stirred slurry of 4.1 g of pentane washed sodium hydride in 100 ml of tetrahydrofuran was treated with 9.1 g of 2-amino-6-methylpyridine and immersed in an ultrasonic bath for 1.5 hours. The stirred slurry was then treated with a solution of 10 g of 4-hydroxy-1-phenyl-3-isoquinolinecarboxylic acid, ethyl ester in 50 ml of tetrahydrofuran and refluxed overnight. Thereafter, the reaction mixture was cooled to room temperature and quenched with water. The resulting precipitate was collected, dried, and solubilized in 300 ml of a 1:1 solution of methanol-water. Carbon dioxide gas was bubbled through the solution until a pH of 7.5 was reached. The resulting precipitate was collected, dried, and recrystallized from dichloromethane to afford 8.4 g (69%)

of 4-hydroxy-N-(6-methyl-2-pyridyl)-1-phenyl-3-isoquinolinecarboxamide, m.p. 261°–263° C.

ANALYSIS: Calculated for $C_{22}H_{17}N_3O_2$: 74.34%C; 4.82%H; 11.82%N; Found: 74.12%C; 4.98%H; 11.73%N.

EXAMPLE 3

N-(3-Chlorophenyl)-4-hydroxy-1-phenyl-3-isoquinolinecarboxamide

A stirred slurry of 4.08 g of hexane washed sodium hydride in 150 ml of dry tetrahydrofuran was treated with a solution of 10.8 g of 3-chloroaniline in 10 ml of tetrahydrofuran and immersed in an ultrasonic bath for 30 minutes. The stirred slurry was then treated with 10 g of 4-hydroxy-1-phenyl-3-isoquinolinecarboxylic acid, ethyl ester and refluxed for 10 hours. Thereafter, the reaction mixture was cooled to room temperature and quenched with water. Recrystallization of the resulting precipitate from ethyl acetate followed by further recrystallization from acetone afforded 6.1 g (48%) of N-(3-chlorophenyl)-4-hydroxy-1-phenyl-3-isoquinolinecarboxamide, m.p. 195°–197° C.

ANALYSIS: Calculated for $C_{22}H_{15}ClN_2O_2$: 70.49%C; 4.03%H; 7.47%N; Found: 70.68%C; 4.07%H; 7.66%N.

EXAMPLE 4

N-(5-Chloro-2-pyridyl)-4-hydroxy-1-phenyl-3-isoquinolinecarboxamide

A stirred slurry of 2.3 g of sodium hydride in 100 ml of dry tetrahydrofuran was treated with 6.1 g of 2-amino-5-chloropyridine and immersed in an ultrasonic bath for 30 minutes. The stirred slurry was then treated with a solution of 7.0 g of 4-hydroxy-1-phenyl-3-isoquinolinecarboxylic acid, ethyl ester in 70 ml of tetrahydrofuran and refluxed for 16 hours. Thereafter, the solution was cooled to room temperature and quenched with 20 ml of water. The resulting precipitate was solubilized in 500 ml of aqueous methanol and treated with carbon dioxide gas. Recrystallization of the precipitate from 500 ml of warm dimethylformamide afforded 7.5 g (84%) of N-(5-chloro-2-pyridyl)-4-hydroxy-1-phenyl-3-isoquinolinecarboxamide, m.p. 249°–251° C.

ANALYSIS: Calculated for $C_{21}H_{14}ClN_3O_2$: 67.11%C; 3.75%H; 11.18%N; Found: 67.28%N; 4.03%H; 11.19%N.

EXAMPLE 5

1,2-Dihydro-4-hydroxy-1-phenyl-N-(2-pyridyl)-3-quinolinecarboxamide

Step 1

A solution of 29 g of 2,3-dihydro-1-phenyl-4(1H)-quinolone in 200 ml of benzene was added, dropwise, to a stirred slurry of 7.2 g of sodium hydride in 200 ml of benzene. The slurry was stirred for one hour at room temperature, and then treated with 23.6 g of diethylcarbonate. The resulting suspension was refluxed for five hours, cooled to room temperature, and quenched with 200 ml of water. The organic phase was separated, dried over anhydrous magnesium sulfate, filtered, and evaporated. Purification of the residue by means of high pressure liquid chromatography (silica gel; dichloromethane as the eluent) afforded 22.4 g (59%) of 1,2-dihydro-4-hydroxy-1-phenyl-3-quinolinecarboxylic acid, ethyl ester. Recrystallization from diethyl ether yielded the analytical sample, m.p. 103°–106° C.

ANALYSIS: Calculated for $C_{18}H_{17}NO_3$: 73.19%C; 5.80%H; 4.74%N; Found: 72.95%C; 5.83%H; 4.67%N.

Step 2

A solution of 2.8 g of 2-aminopyridine and 4.2 g of 1,2-dihydro-4-hydroxy-1-phenyl-3-quinolinecarboxylic acid, ethyl ester in 190 ml of toluene was refluxed for 16 hours in a soxhlet apparatus containing 10 g of 4Å molecular sieves. Evaporation of the volatiles afforded a residue which was purified by means of high pressure liquid chromatography (silica gel: 1:1 ethyl acetate-hexane as the eluent) to yield 3.7 g (73%) of 1,2-dihydro-4-hydroxy-1-phenyl-N-(2-pyridyl)-3-quinolinecarboxamide, m.p. 145° C. (dec).

ANALYSIS: Calculated for $C_{21}H_{17}N_3O_2$: 73.45%C; 4.99%H; 12.23%N; Found: 73.45%C; 5.03%H; 12.16%N.

EXAMPLE 6

1,2-Dihydro-4-hydroxy-N-(5-methyl-3-isoxazolyl)-1-phenyl-3-quinolinecarboxamide A solution of 2.0 g of 3-amino-5-methylisoxazole and 5.5 g of 1,2-dihydro-4-hydroxy-1-phenyl-3-quinolinecarboxylic acid, ethyl ester in 260 ml of toluene was refluxed for 10 hours in a soxhlet apparatus containing 10 g of 4Å molecular sieves. Evaporation of the volatiles afforded a residue which was purified by means of high pressure liquid chromatography (silica gel: 3:1 ethyl acetate-hexane as the eluent) to yield 3.5 g (51%) of 1,2-dihydro-4-hydroxy-N-(5-methyl-3-isoxazolyl)-1-phenyl-3-quinolinecarboxamide. Recrystallization from dichloromethane afforded the analytical sample, m.p. 148°–150° C.

ANALYSIS: Calculated for $C_{20}H_{17}N_3O_3$: 69.15%C; 4.93%H; 12.09%N; Found: 69.16%C; 5.16%H; 11.89%N.

EXAMPLE 7

1,2-Dihydro-4-hydroxy-1-phenyl-N-(2-thiazolyl)-3-quinolinecarboxamide

A solution of 4.08 g of 2-aminothiazole and 8.0 g of 1,2-dihydro-4-hydroxy-1-phenyl-3-quinolinecarboxylic acid, ethyl ester in 250 ml of toluene was refluxed for 30 hours in a soxhlet apparatus containing 10 g of 4Å molecular sieves. Evaporation of the volatiles afforded a residue which was purified by means of high pressure liquid chromatography (silica gel: 1:25 ethyl acetate-dichloromethane as the eluent). The resultant solution was degassed and evaporated. Recrystallization of the residue from diethyl ether yielded 6.35 g (67%) of 1,2-dihydro-4-hydroxy-1-phenyl-N-(2-thiazolyl)-3-quinolinecarboxamide, m.p. 220° C. (dec.).

ANALYSIS: Calculated for $C_{19}H_{15}N_3O_2S$: 65.31%C; 4.33%H; 12.03%N; Found: 65.14%C; 4.35%H; 11.96%N.

EXAMPLE 8

1,2-Dihydro-4-hydroxy-1-phenyl-N-phenyl-3-quinolinecarboxamide

A solution of 12.63 g of aniline and 10.0 g of 1,2-dihydro-4-hydroxy-1-phenyl-3-quinolinecarboxylic acid, ethyl ester in 250 ml of toluene was refluxed for 24 hours in a soxhlet apparatus containing 10 g of 4Å molecular sieves. Evaporation of the volatiles afforded a residue which was purified by means of high pressure liquid chromatography (silica gel: dichloromethane as the eluent). The resultant solution was degassed and evaporated. Recrystallization of the residue from diethyl ether yielded 7.55 g (65%) of 1,2-dihydro-4-hydroxy-1-phenyl-N-phenyl-3-quinolinecarboxamide, m.p. 120° C.

ANALYSIS: Calculated for $C_{22}H_{18}N_2O_2$: 77.17%C; 5.30%H; 8.18%N; Found: 77.37%C; 5.42%H; 8.16%N.

EXAMPLE 9

1,2-Dihydro-4-hydroxy-1-phenyl-N-(2-pyrazinyl)-3-quinolinecarboxamide

A solution of 12.08 g of 2-aminopyrazine and 25.0 g of 1,2-dihydro-4-hydroxy-1-phenyl-3-quinolinecarboxylic acid, ethyl ester in 500 ml of toluene was refluxed for 24 hours in a soxhlet apparatus containing 20 g of 4Å molecular sieves. Evaporation of the volatiles afforded a residue which was purified by means of high pressure liquid chromatography (silica gel: 4% ethyl acetate-dichloromethane as the eluent). The resultant solution was degassed and evaporated. Recrystallization of the residue from diethyl ether yielded 13.15 g (45%) of 1,2-dihydro-4-hydroxy-1-phenyl-N-2-(pyrazinyl)-3-quinolinecarboxamide, m.p. 184°–186° C.

ANALYSIS: Calculated for $C_{20}H_{16}N_4O_2$: 69.75%C; 4.68%H; 16.27%N; Found: 69.38%C; 4.51%H; 16.25%N.

EXAMPLE 10

1,2-Dihydro-4-hydroxy-N-(4-methyl-2-thiazolyl)-1-phenyl-3-quinolinecarboxamide

A solution of 14.5 g of 2-amino-4-methylthiazole and 25.0 g of 1,2-dihydro-4-hydroxy-1-phenyl-3-quinolinecarboxylic acid, ethyl ester in 250 ml of toluene was refluxed for 24 hours in a soxhlet apparatus containing 20 g of 4Å molecular sieves. Evaporation of the volatiles afforded a residue which was purified by means of high pressure liquid chromatography (silica gel: 2% diethyl ether-dichloromethane as the eluent) followed by recrystallization from diethyl ether to yield 20.7 g (67%) of 1,2-dihydro-4-hydroxy-N-(4-methyl-2-thiazolyl)-1-phenyl-3-quinolinecarboxamide, m.p. 228°–230° C.

ANALYSIS: Calculated for $C_{20}H_{17}N_3O_2S$: 66.09%C; 4.72%H; 11.56%N; Found: 65.78%C; 4.78%H; 11.42%N.

EXAMPLE 11

1,2-Dihydro-4-hydroxy-N-(6-methyl-2-pyridyl)-1-phenyl-3-quinolinecarboxamide

A solution of 5.49 g of 2-amino-6-methylpyridine and 10.0 g of 1,2-dihydro-4-hydroxy-1-phenyl-3-quinolinecarboxylic acid, ethyl ester in 250 ml of toluene was refluxed overnight in a soxhlet apparatus containing 10 g of 4Å molecular sieves. Evaporation of the volatiles afforded a residue which was purified by means of high pressure liquid chromatography (silica gel: 2% ethyl acetate-dichloromethane). The resultant solution was degassed and evaporated. Recrystallization of the residue from diethyl ether yielded 5.30 g (43%) of 1,2-dihydro-4-hydroxy-N-(6-methyl-2-pyridyl)-1-phenyl-3-quinolinecarboxamide, m.p. 74°–77° C.

ANALYSIS: Calculated for $C_{22}H_{19}N_3O_2$: 73.93%C; 5.36%H; 11.76%N; Found: 74.08%C; 5.59%H; 11.82%N.

EXAMPLE 12

N-(5-Bromo-2-pyridyl)-1,2-dihydro-4-hydroxy-1-phenyl-3-quinolinecarboxamide

A solution of 21.98 g of 2-amino-5-bromopyridine and 25.0 g of 1,2-dihydro-4-hydroxy-1-phenyl-3-quinolinecarboxylic acid, ethyl ester in 250 ml of toluene was refluxed for 24 hours in a soxhlet apparatus containing 20 g of 4Å molecular sieves. Evaporation of the volatiles afforded a residue which was purified by means of high pressure liquid chromatography (silica gel: dichloromethane as the eluent). The resultant solution was degassed and evaporated to yield 23.56 g (66%) of N-(5-bromo-2-pyridyl)-1,2-dihydro-4-hydroxy-1-phenyl-3-quinolinecarboxamide, m.p. 153°–154° C.

ANALYSIS: Calculated for $C_{21}H_{16}BrN_3O_2$: 59.73%C; 3.82%H; 9.95%N; Found: 59.67%C; 3.92%H; 9.84%N.

EXAMPLE 13

1,4-Dihydro-4-oxo-1-phenyl-N-(2-pyridyl)-3-quinolinecarboxamide

A solution of 2.4 g of 1,2-dihydro-4-hydroxy-1-phenyl-N-(2-pyridyl)-3-quinolinecarboxamide in 150 ml of benzene was treated with 8.4 g of activated manganese dioxide. The slurry was stirred at room temperature for 30 minutes, filtered, and evaporated. Recrystallization of the residue from dichloromethane-diethyl ether afforded 2.19 g (92%) of 1,4-dihydro-4-oxo-1-phenyl-N-(2-pyridyl)-3-quinolinecarboxamide, m.p. 238°–240° C.

ANALYSIS: Calculated for $C_{21}H_{15}N_3O_2$: 73.88%C; 4.42%H; 12.30%N; Found: 73.53%C; 4.44%H; 12.18%H.

EXAMPLE 14

1,4-Dihydro-N-(5-methyl-3-isoxazolyl)-4-oxo-1-phenyl-3-quinolinecarboxamide

A solution of 6.0 g of 3-amino-5-methylisoxazole and 10 g of 1,2-dihydro-4-hydroxy-1-phenyl-3-quinolinecarboxylic acid, ethyl ester in 150 ml of toluene was refluxed for 16 hours in a soxhlet apparatus containing 10 g of 4Å molecular sieves. The solution was cooled to room temperature, treated with 30 g of activated manganese dioxide, stirred for three hours at 30° C., and filtered. Evaporation of the volatiles afforded a residue which was purified by means of high pressure liquid chromatography (silica gel: 1% methanol-dichloromethane as the eluent) to yield 5.8 (49%) of 1,4-dihydro-N-(5-methyl-3-isoxazolyl)-4-oxo-1-phenyl-3-quinolinecarboxamide, m.p. 163°–164° C.

ANALYSIS: Calculated for $C_{20}H_{15}N_3O_3$: 69.55%C; 4.37%H; 12.16%N; Found: 69.40%C; 4.32%H; 12.10%N.

EXAMPLE 15

1,4-Dihydro-4-oxo-1-phenyl-N-(2-thiazolyl)-3-quinolinecarboxamide

To a stirred solution of 6.67 g of 1,2-dihydro-4-hydroxy-1-phenyl-N-(2-thiazolyl)-3-quinolinecarboxamide in 100 ml of dichloromethane was added, dropwise, a solution of 26.7 g of barium permanganate in 500 ml of dichloromethane. After stirring for six hours at room temperature the solution was filtered and evaporated. Recrystallization of the residue from chloroform yielded 5.70 g (86%) of 1,4-dihydro-4-oxo-1-phenyl-N-(2-thiazolyl)-3-quinolinecarboxamide, m.p. 290° C.

ANALYSIS: Calculated for $C_{19}H_{14}N_3O_2S$: 65.70%C; 4.06%H; 12.10%N; Found: 65.44%C; 3.82%H; 12.19%N.

EXAMPLE 16

1,4-Dihydro-4-oxo-1-phenyl-N-phenyl-3-quinolinecarboxamide

A solution of 15.0 g of 1,2-dihydro-4-hydroxy-1-phenyl-N-phenyl-3-quinolinecarboxamide in 250 ml of toluene was treated with 60.0 g of activated manganese dioxide and stirred at room temperature for four hours. The slurry was filtered and evaporated. The residue was purified first by flash chromatography (silica gel: dichloromethane as eluent), and then by high pressure liquid chromatography (silica gel: dichloromethane). Recrystallization of the residue from dichloromethane yielded 6.75 g (45%) of 1,4-dihydro-4-oxo-1-phenyl-N-phenyl-3-quinolinecarboxamide, m.p. 203°–205° C.

ANALYSIS: Calculated for $C_{22}H_{16}N_2O_2$: 77.63%C; 4.74%H; 8.23%N; Found: 77.21%C; 4.83%H; 8.18%N.

EXAMPLE 17

1,4-Dihydro-4-oxo-1-phenyl-N-(2-pyrazinyl)-3-quinolinecarboxamide

A solution of 8.0 g of 1,2-dihydro-4-hydroxy-1-phenyl-N-(2-pyrazinyl)-3-quinolinecarboxamide in 250 ml of chloroform was treated with 33.0 g of activated manganese dioxide and stirred for six hours at room temperature. The slurry was filtered and evaporated. Recrystallization of the residue from chloroform yielded 5.46 g (90%) of 1,4-dihydro-4-oxo-1-phenyl-N-(2-pyrazinyl)-3-quinolinecarboxamide, m.p. 298°–300° C.

ANALYSIS: Calculated for $C_{20}H_{14}N_4O_2$: 70.16%C; 4.12%H; 16.37%N; Found: 69.52%C; 4.21%H; 16.33%N.

EXAMPLE 18

1,4-Dihydro-N-(4-methyl-2-thiazolyl)-4-oxo-1-phenyl-3-quinolinecarboxamide

A solution of 9.0 g of 1,2-dihydro-4-hydroxy-N-(4-methyl-2-thiazolyl)-1-phenyl-3-quinolinecarboxamide in 250 ml of hot toluene was treated with 36.0 g of activated manganese dioxide and stirred for two hours at ambient temperature. The slurry was filtered and evaporated. Recrystallization of the residue from chloroform yielded 6.0 g (66%) of 1,4-dihydro-N-(4-methyl-2-thiazolyl)-4-oxo-1-phenyl-3-quinolinecarboxamide, m.p. 252°–254° C.

ANALYSIS: Calculated for $C_{20}H_{16}N_3O_2S$: 66.46%C; 4.46%H; 11.63%N; Found: 66.16%C; 4.35%H; 11.29%N.

EXAMPLE 19

1,4-Dihydro-N-(6-methyl-2-pyridyl)-4-oxo-1-phenyl-3-quinolinecarboxamide

A solution of 5.49 g of 2-amino-6-methylpyridine and 10 g of 1,2-dihydro-4-hydroxy-1-phenyl-3-quinolinecarboxylic acid, ethyl ester in 500 ml of toluene was refluxed for 24 hours in a soxhlet apparatus containing 10 g of 4Å molecular sieves. The solution was filtered and evaporated. The residue was purified by means of high pressure liquid chromatography (silica gel: dichloromethane as the eluent) to afford 9.8 g of 1,2-dihydro-4-hydroxy-N-(6-methyl-2-pyridyl)-1-phenyl-3-quinolinecarboxamide which was dissolved in chloroform, treated with 35 g of activated manganese dioxide and stirred for three hours at room temperature.

The slurry was filtered and evaporated. Recrystallization of the residue from diethyl ether yielded 5.8 g (24%) of 1,4-dihydro-N-(6-methyl-2-pyridyl)-4-oxo-1-phenyl-3-quinolinecarboxamide, m.p. 273°–274° C.

ANALYSIS: Calculated for $C_{22}H_{17}N_3O_2$: 74.38%C; 4.82%H; 11.81%N; Found: 74.15%C; 4.90%H; 11.77%N.

EXAMPLE 20

1,4-Dihydro-N-(5-methyl-2-pyridyl)-4-oxo-1-phenyl-3-quinolinecarboxamide

A solution of 12.30 g of 1,2-dihydro-4-hydroxy-N-(5-methyl-2-pyridyl)-1-phenyl-3-quinolinecarboxamide in 250 ml of chloroform was treated with 50.0 g of activated manganese dioxide and stirred at room temperature for two hours. The slurry was filtered and evaporated. Recrystallization of the residue from chloroform yielded 10.96 g (91%) of 1,4-dihydro-N-(5-methyl-2-pyridyl)-4-oxo-1-phenyl-3-quinolinecarboxamide, m.p. 248°–250° C.

ANALYSIS: Calculated for $C_{22}H_{17}N_3O_2$: 74.35%C; 4.82%H; 11.82%N; Found: 74.54%C; 5.00%H; 11.85%N.

EXAMPLE 21

N-(2-benzothiazolyl)-1,4-dihydro-4-oxo-1-phenyl-3-quinolinecarboxamide

A solution of 9.66 g of N-(2-benzothiazolyl)-1,2-dihydro-4-hydroxy-1-phenyl-3-quinolinecarboxamide in 250 ml of toluene was treated with 39.0 g of activated manganese dioxide and stirred for four hours at room temperature. The slurry was filtered and evaporated. The residue was purified by means of high pressure liquid chromatography (silica gel: dichloromethane as the eluent) followed by recrystallization from dichloromethane to yield 4.6 g (48%) of N-(2-benzothiazolyl)-1,4-dihydro-4-oxo-1-phenyl-3-quinolinecarboxamide, m.p. 295°–297° C.

ANALYSIS: Calculated for $C_{23}H_{15}N_3O_2S$: 69.50%C; 3.80%H; 10.57%N; Found: 69.22%C; 3.98%H; 10.50%N.

REACTION SCHEME A
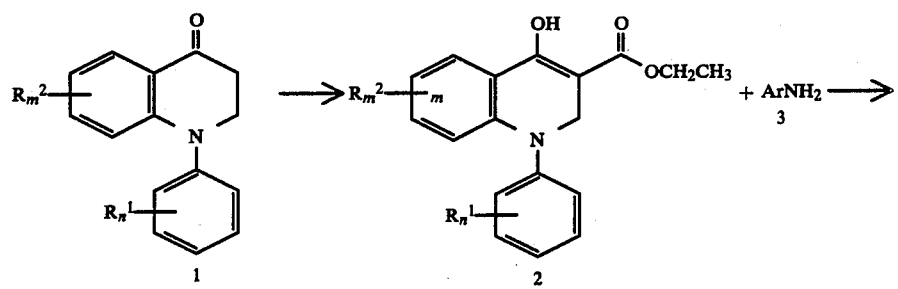
wherein $R^1$, $R^2$, m and n are as previously defined; and Ar is an aromatic radical $R^3$ as previously defined.
6a
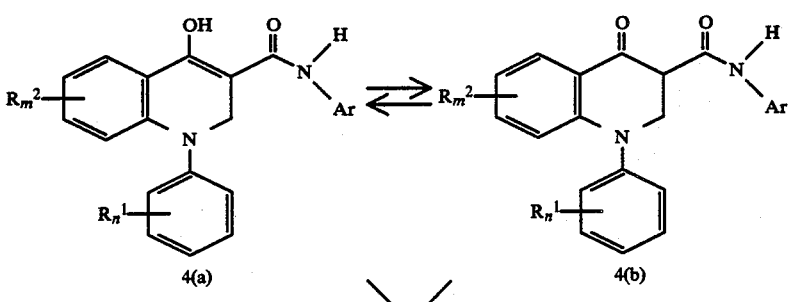
4(a)            4(b)
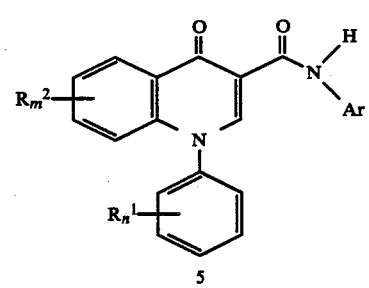
5
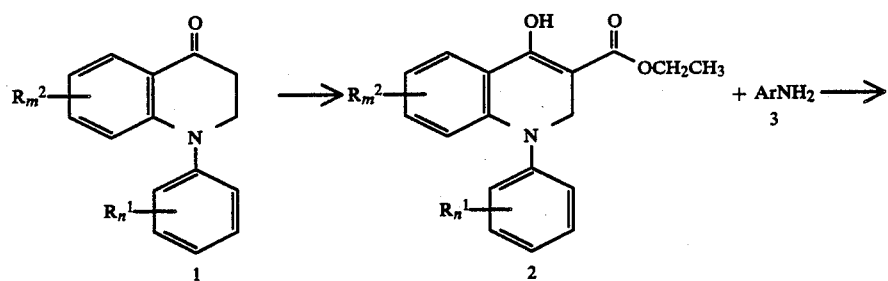
wherein $R^1$, $R^2$, m and n are as previously defined; and Ar is an aromatic radical $R^3$ as previously defined.
6a

REACTION SCHEME A
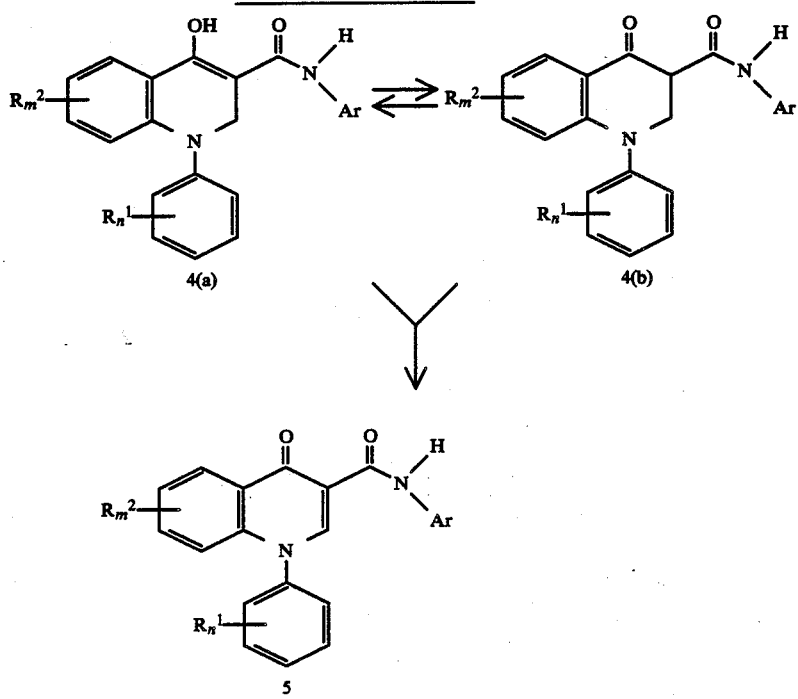
REACTION SCHEME B
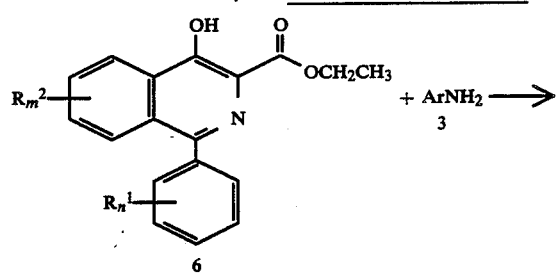
wherein $R^1$, $R^2$, m and n are as previously defined; and Ar is an aromatic radical $R^3$ as previously defined.
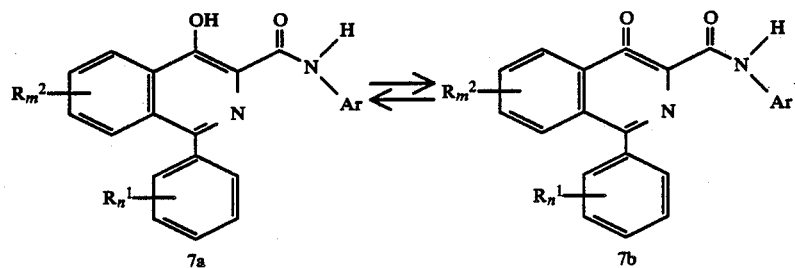
What is claimed is:
1. A compound of the formula:

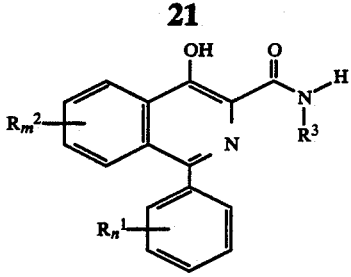

wherein $R^1$ and $R^2$ are monovalent radicals independently selected form the group consisting of halogen, loweralkyl and loweralkoxy; $R^3$ is substituted or unsubstituted monovalent radical selected from the group consisting of phenyl and pyridyl, and m and n are integers independently having values of zero or 1; the optical antipodes and pharmaceutically acceptable acid addition salts thereof.

2. A compound as defined in claim 1 wherein $R^3$ is a phenyl radical of the formula:

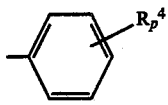

wherein $R^4$ is a radical selected from the group consisting of loweralkyl, loweralkoxy, trifluoromethyl, nitro, or halogen and p is an integer having a value from zero to 4, inclusive, wherein for each value of p, $R^4$ may be the same or different.

3. A compound as defined in claim 1 wherein $R^3$ is a pyridyl radical of the formula:

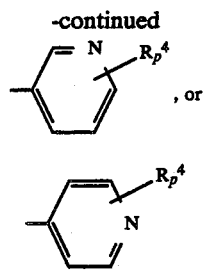

wherein $R^4$ is a radical selected from the group consisting of loweralkyl, loweralkoxy, or halogen, and p is an integer having a value from zero to 4 inclusive, wherein for each value of p, $R^4$ may be the same or different.

4. A compound as defined in claim 1 wherein $R^3$ is selected from the group consisting of substituted and unsubstituted phenyl and pyridyl radicals.

5. A compound as defined in claim 1 wherein m and n are zero.

6. The compound of claim 3 which is 4-hydroxy-1-phenyl-N-(2-pyridyl)-3-quinolinecarboxamide.

7. The compound of claim 3 which is N-(5-chloro-2-pyridyl)-4-hydroxy-1-phenyl-3-isoquinolinecarboxamide.

8. The compound of claim 3 which is 4-hydroxy-N-(6-methyl-2-pyridyl)-1-phenyl-3-isoquinolinecarboxamide.

9. The compound of claim 2 which is N-(3-chlorophenyl)-4-hydroxy-1-phenyl-3-isoquinolinecarboxamide.

10. A method of alleviating pain comprising administering to a mammal in need of pain alleviation a pain alleviating effective amount of a compound as defined in claim 1.

11. A pain alleviating composition comprising an inert adjuvant and, as the active ingredient, an amount effective in alleviating pain of a compound as defined in claim 1.

12. A method of inhibiting inflammation comprising administering to a mammal in need of inflammation inhibition an inflammation inhibiting effective amount of a compound as defined in claim 1.

13. An inflammation inhibiting composition comprising an inert adjuvant and, as the active ingredient, an amount effective in inhibiting inflammation of a compound as defined in claim 1.

* * * * *